(12) United States Patent
Sharifalhosseini et al.

(10) Patent No.: US 10,687,820 B2
(45) Date of Patent: Jun. 23, 2020

(54) UNILATERAL SPINAL CORD COMPRESSION

(71) Applicants: Mahdi Sharifalhosseini, Tehran (IR); Vafa Rahimimovaghar, Tehran (IR)

(72) Inventors: Mahdi Sharifalhosseini, Tehran (IR); Vafa Rahimimovaghar, Tehran (IR)

(*) Notice: Subject to any disclaimer, the term of this patent is extended or adjusted under 35 U.S.C. 154(b) by 411 days.

(21) Appl. No.: 15/410,670

(22) Filed: Jan. 19, 2017

(65) Prior Publication Data
US 2017/0132952 A1    May 11, 2017

Related U.S. Application Data

(60) Provisional application No. 62/286,320, filed on Jan. 23, 2016.

(51) Int. Cl.
| | |
|---|---|
| A61B 17/12 | (2006.01) |
| B25B 5/06 | (2006.01) |
| B25B 5/10 | (2006.01) |
| A61B 17/122 | (2006.01) |
| B25B 5/16 | (2006.01) |
| G09B 23/30 | (2006.01) |
| G09B 23/32 | (2006.01) |
| G09B 23/34 | (2006.01) |
| A01K 29/00 | (2006.01) |
| A61D 1/00 | (2006.01) |
| A01K 67/027 | (2006.01) |

(52) U.S. Cl.
CPC ............ *A61B 17/12* (2013.01); *A61B 17/122* (2013.01); *B25B 5/068* (2013.01); *B25B 5/102* (2013.01); *B25B 5/166* (2013.01); *A01K 29/005* (2013.01); *A01K 67/027* (2013.01); *A01K 2207/30* (2013.01); *A01K 2227/105* (2013.01); *A01K 2227/107* (2013.01); *A01K 2267/035* (2013.01); *A61D 1/00* (2013.01); *G09B 23/306* (2013.01); *G09B 23/32* (2013.01); *G09B 23/34* (2013.01)

(58) Field of Classification Search
CPC ........... B25B 5/067; B25B 5/068; B25B 5/10; B25B 5/101; B25B 5/102; B25B 5/166; A61B 17/12
See application file for complete search history.

(56) References Cited

U.S. PATENT DOCUMENTS

| | | | |
|---|---|---|---|
| 6,722,643 B1 * | 4/2004 | Kurtz | ........................ B25B 5/10 269/249 |
| 7,753,054 B2 | 7/2010 | Okano et al. | |

OTHER PUBLICATIONS

Joseph S. Soblosky, Graded unilateral cervical spinal cord injury in the rat: evaluation of forelimb recovery and histological effects, Behavioural Brain Research, Sep. 2000, vol. 119, pp. 1-13.
Jae H.T. Lee, A Contusive Model of Unilateral Cervical Spinal Cord Injury Using the Infinite Horizon Impactor, Journal of Visualized Experiments, Jul. 2012, vol. 65.

(Continued)

*Primary Examiner* — William H Matthews
(74) *Attorney, Agent, or Firm* — Bajwa IP Law Firm; Haris Zaheer Bajwa (57) ABSTRACT

An apparatus for unilateral spinal cord compression includes a fixed member and a movable member that moves longitudinally along the fixed member by using a linear actuating mechanism to compress a portion of spinal cord encompassed by the movable member and the fixed member.

10 Claims, 11 Drawing Sheets

(56) References Cited

OTHER PUBLICATIONS

John C. Gensel, Behavioral and Histological Characterization of Unilateral Cervical Spinal Cord Contusion Injury, Journal of Neurotrauma, Jan. 2006, vol. 23, No. 1, pp. 36-54.
Hiroshi Ozawa, Morphologic Change and Astrocyte Response to Unilateral Spinal Cord Compression in Rabbits, Journal of Neurotrauma, vol. 21, No. 7, pp. 944-955.

* cited by examiner

UNILATERAL SPINAL CORD COMPRESSION

CROSS REFERENCE TO RELATED APPLICATION

The present application claims priority from U.S. Provisional Patent Application Ser. No. 62/286,320, filed Jan. 23, 2016, entitled "UNILATERAL SPINAL CORD COMPRESSION DEVICE", which is incorporated by reference herein in its entirety.

TECHNICAL FIELD

The present application generally relates to an apparatus for unilateral spinal cord compression and a method for use thereof to simulate spinal cord injuries (hereinafter "SCI") in an animal model.

BACKGROUND

Traumatic spinal cord injury (hereinafter "SCI") is a devastating clinical condition afflicting thousands of individuals each year worldwide, for which no appropriate treatment has so far been developed. The ongoing development of SCI animal models reflect the persistent need for a better mimic of human injury in order to reliably investigate neuro-physiological mechanisms, pathology and potential therapies.

Approximately, more than half of the human SCI cases affect cervical regions, resulting in impairments of motor functions of the upper extremity. Even modest recovery of upper extremity function could have a vast impact on quality of life for quadriplegics. High cervical level injuries can result in diaphragm dysfunction due to interruption of bulbospinal respiratory drive to Phrenic Motor Neurons pools (C3-C6). An essential feature of cervical SCI models is that they must be incomplete to preserve an adequate degree of function to allow survival of animals.

Different models of the injury in human SCIs are compression, contusion, laceration, transaction, dislocation, distraction and traction of the spinal cord. Since the most of the human traumatic SCIs occur as a result of vertebral fractures or dislocations, the most clinically relevant injury models are those, in which spinal cord is compressed. Compression models contribute to simulating persistent spinal canal occlusion that is common in human SCIs and investigating the effects of compression or optimal timing of decompression.

Thus, there is a major need to develop experimental models and methods applicable in animal models for simulating human cervical SCIs to evaluate shortages and recovery of the forelimb motor function. More specifically, there is a need for a unilateral compressive SCI model to compress exactly half of the spinal cord of an animal model and preserving animal survival during subsequent studies and experiments.

SUMMARY

Disclosed aspects include example apparatuses for unilateral spinal cord compression. One or more examplary apparatuses that are disclosed include a fixed member and a movable member that can move longitudinally along the fixed member using a linear actuating mechanism to compress a portion of a spinal cord encompassed by the movable member and the fixed member.

Example implementations may include one or more of the following features. For example, in one implementation, the fixed member can include a fixed arm having two ends and a planar member, and in an aspect the planar member can be fixed from the middle onto the second end of the fixed arm.

In one and more example implementations, the movable member can include a plate parallel to the planar member having a lateral slit to pass the fixed arm. In an aspect, the moveable member can be configured to compress an encompassed portion of a spinal cord (half of a spinal cord or less) by the movable member and the curved base.

The linear actuating mechanism may include a fastener, a first coupler, and a second coupler. In some implementations, the linear actuating mechanism can be configured to cause the movable member to move longitudinally along the fixed arm, resulting in compressing a portion of spinal cord encompassed by the movable member and the curved base.

In some example implementation, the fixed member and the movable member may be made of a metal or metal alloy sheet, for example stainless steel, passificated stainless steel grade 314 or gold with a thickness of less than about 1 mm. In some example implementation, the fastener can be selected from a group of a screw, a twist, a rivet, and a bolt. The first coupler may include an internal threaded member or a screw nut and the second coupler may include a ball bearing.

Implementations can also include an apparatus for unilateral spinal cord compression, comprising an arm, having a curved base end and an upper end; a planar member fixed to the arm, the planar member being fixed to the arm at a location proximal the upper end, and can include a movable member, comprising a plate that extends parallel to the planar member, and that includes a lateral opening through which the fixed arm can extend. In an implementation the apparatus can include a first coupler, secured to the planar member, a second coupler, secured to the movable member; a rotatable member, having a distal end and coupled by the first coupler to the planar member in a coupling configuration wherein rotating the rotatable member in a given direction can move the distal end relative to the planar member in a direction toward the curved base end, wherein the distal end can be coupled by the second coupler to the movable member in a configuration wherein movement of the distal end toward the curved base end moves the movable member toward the curved base end.

In another general aspect of the present disclosure, a method directed to unilateral spinal cord injury (SCI) in an animal is disclosed. The exemplary method may include the steps of providing an access to the spine of the animal, removing delicate bones in the posterior lamina to expose the spinal cord, encompassing a portion of the exposed spinal cord between a fixed member and a movable member of an apparatus designed for unilateral spinal cord compression, compressing the encompassed portion of the exposed spinal cord of the animal in a way that up to half of the spinal cord encompassed by the apparatus to be compressed. In one exemplary implementation, the animal may include a mammal animal, for example rabbits, rats, etc.

In some exemplary implementation, the access to the spine may be provided via performing a surgery in the back of the animal.

In some exemplary implementation, the covering and compressing up to half of the spinal cord of the animal may be done using an apparatus disclosed in the present disclosure configured for unilateral spinal cord compression.

In one and more implementations, compressing up to half of the spinal cord can be achieved by turning the fastener manually in the proper direction for moving downward the movable plate result in compressing the encompassed portion of the spinal cord. In related implementations, the unilateral spinal cord compression can be obtained in various grades of severity and the various grade of severity is controlled by changing the number of turning rotations of the fastener.

DETAILED DESCRIPTION

The following detailed description is presented to enable a person skilled in the art to make and use the application. For purposes of explanation, specific nomenclature is set forth to provide a thorough understanding of the present application. However, it will be apparent to one skilled in the art that these specific details are not required to practice the application. Descriptions of specific applications are provided only as representative examples. Various modifications to the preferred implementations will be readily apparent to one skilled in the art, and the general principles defined herein may be applied to other implementations and applications without departing from the scope of the application. The present application is not intended to be limited to the implementations shown, but is to be accorded the widest possible scope consistent with the principles and features disclosed herein.

Because of its reliability and reproducibility, the thoracic contusion model has been the most commonly utilized model in studying SCI. However, thoracic SCI models may not be precisely comparable to the cervical SCI. This could be due to differences in distance between cell bodies of injured axons, the amount of grey matter (cells), the absolute number of nerve fibers in the white matter and for the reason that some behaviors (e.g. stepping movements) used to evaluate the therapeutic potential of a given treatment are primarily governed by intra-spinal neuronal circuitry while other behaviors (e.g. skilled reaching) require more sophisticated conscious integration of the sensorimotor system. On the other hand, some of animals (e.g. rats) used as models in clinical studies do not use their hind limbs as proficiently as their forelimbs. Therefore, the overall degree of declination in hind limb paw and digit function cannot be as accurately resolved as a change in function of the forelimb paws and digits. In the same way, recovery from forelimb dysfunction could present more skilled motor movements and consequently a better evaluation of the efficacy of potential treatments, particularly those which may offer only small improvements. Also, it is known that in the instance of partial cervical SCI, the forelimbs appear to be affected more profoundly than the hind limbs.

Disclosed herein is an apparatus and a method for unilateral spinal cord compression to achieve a SCI model applicable for cervical SCI compression as well as thoracic, lumbar, sacral and coccygeal cases. The model animals can be survived during and after such unilateral cervical SCI because of causing only a partially paralysis and remaining some of respiratory tracts. In addition, applying a unilateral SCI provides a possibility of a precise study in a single animal body using the injured half as the patient and the health half as the control model for investigations of SCI affects and the following therapeutic treatments effects.

As used herein, the term "half" as used in statements such as "half of a spinal cord" refers to an exactly half of a cross section of a spinal cord making no restriction about the length of the spinal cord.

In an aspect, the present disclosure describes an apparatus for unilateral spinal cord injury (i.e. spinal cord compression), wherein the apparatus can include a fixed member, a movable member and a linear actuating mechanism, the apparatus may be configured to encompass and compress up to half of a spinal cord. Subsequently, a method for using the apparatus thereof to apply a SCI in an animal model is also disclosed here.

Figure 1A:
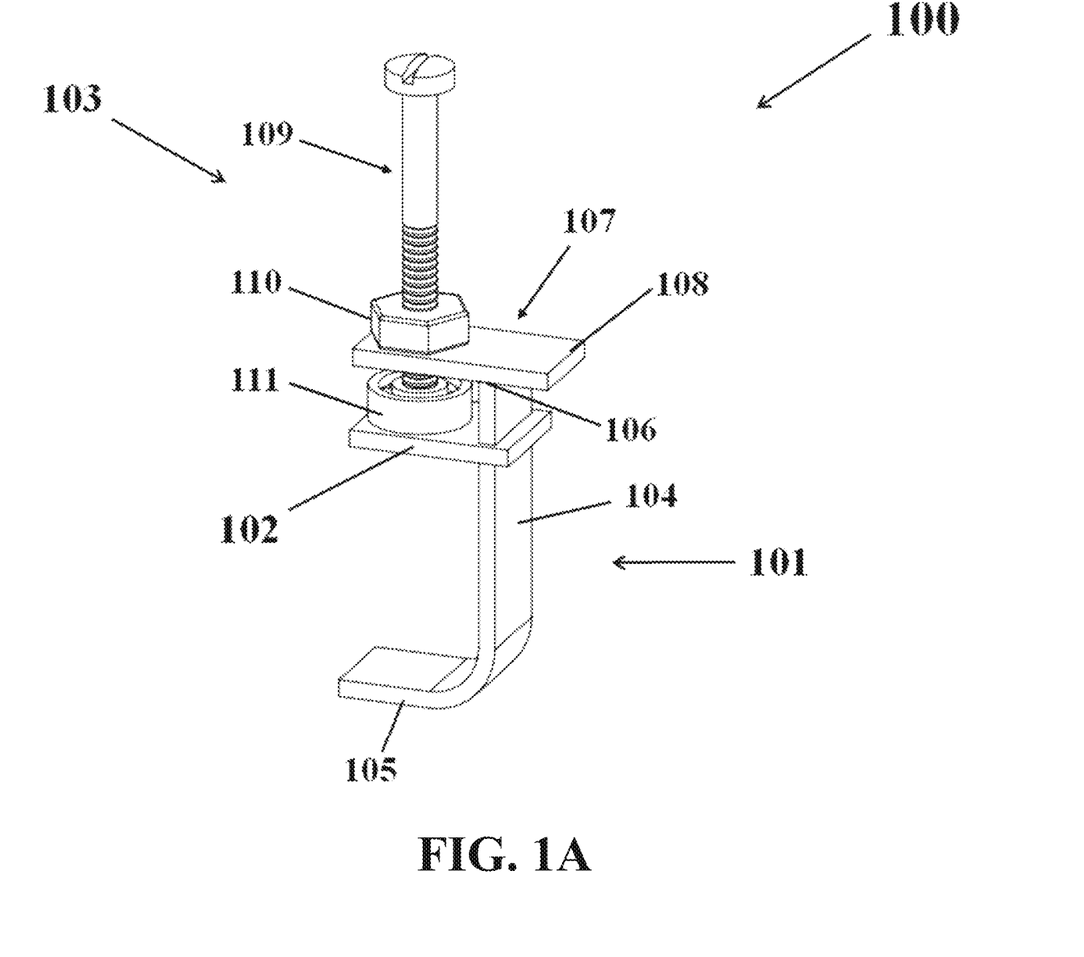
FIG. 1A illustrates a schematic perspective view of an exemplary apparatus for unilateral spinal cord compression, consistent with one or more exemplary embodiments of the present disclosure.
Figure 1B:
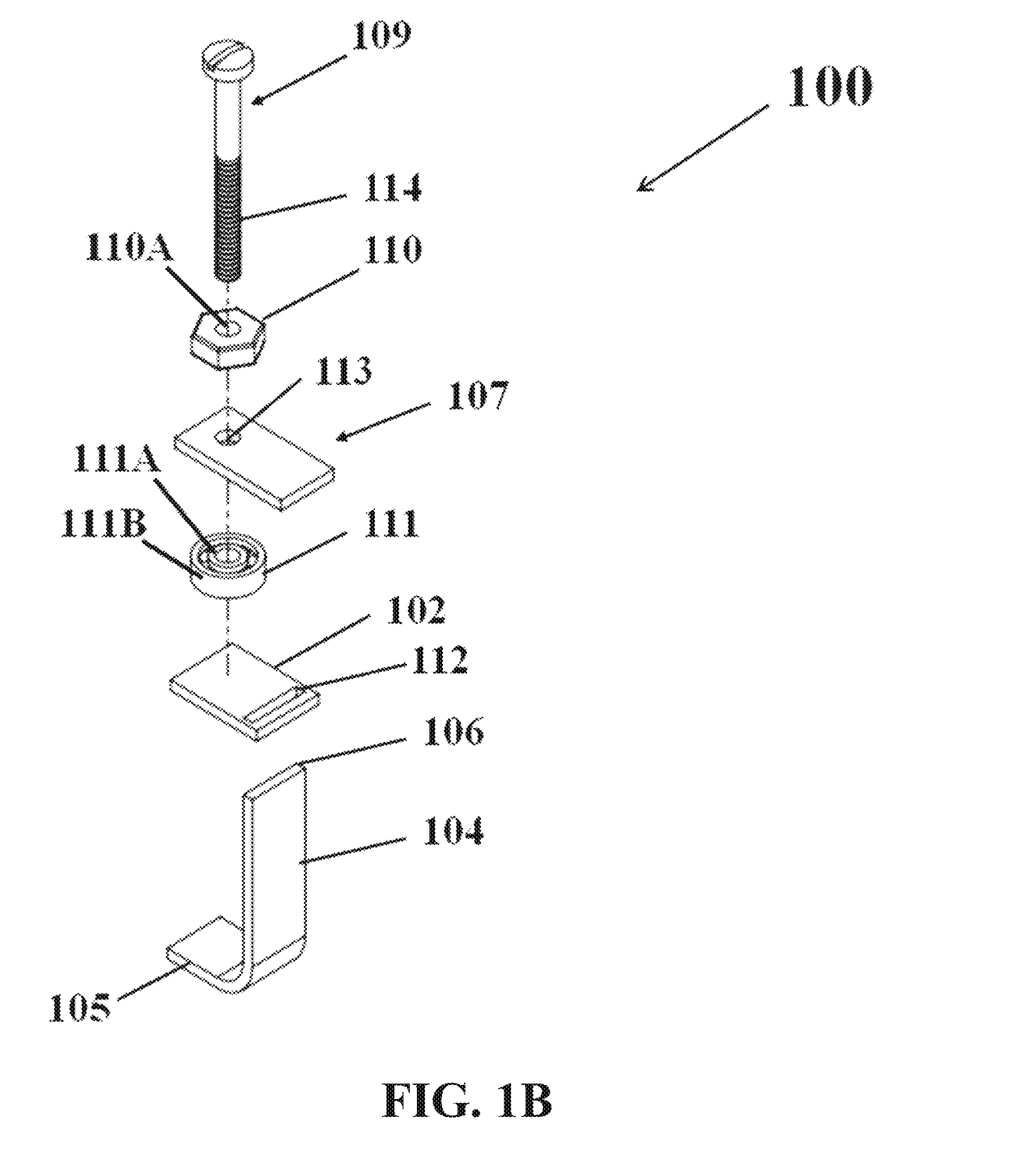
FIG. 1B illustrates an exploded view of one schematic implementation of an exemplary apparatus for unilateral spinal cord compression, consistent with one or more exemplary embodiments of the present disclosure.

FIG. 1A illustrates a perspective schematic image and FIG. 1B illustrates the corresponding exploded schematic image of one example of an apparatus for unilateral spinal cord compression, consistent with one or more exemplary embodiments of the present disclosure according to one or more aspects of the present disclosure. Referring to the implementation shown in FIG. 1A, the apparatus 100 may include a fixed member 101, a movable member 102 and a linear actuating mechanism 103. The fixed member 101 may include a fixed arm 104 having two ends including a first end that may be a curved base 105 and a second end 106, and a planar member 107 fixed from middle onto the second end 106 of the fixed arm 104, over all forming a J-shaped like fixed member 101. The free edge 108 of the planar member 107 may be capable of being engaged by a holder, for example a needle holder, to secure or support the apparatus 100. The movable member 102, the planar member 107 and the curved base 105 may be designed in a parallel configuration as shown in FIG. 1A.

In some implementations, all parts of the apparatus 100 may be made of a metal or metal alloy sheet, for example, gold or stainless steel, and in some particular examples, passificated stainless steel grade 314. The metal or metal alloy sheet used for the fabrication of the fixed member 101 and movable member 102 may have a thickness of about less than 1 mm.

Referring again to FIGS. 1A and 1B, the movable member 102 may include a plate parallel to the planar member 107 having a lateral slit 112 to pass the fixed arm 104. In an implementation, the movable member 102 may be configured to move alongside the fixed arm 104 to compress a portion of an exemplary spinal cord encompassed within the movable member 102 and the curved base 105.

In one implementation, the linear actuating mechanism 103 may be configured to cause the movable member 102 to move upward and downward longitudinally along the fixed arm 104 to compress a portion of an exemplary spinal cord placed between the movable member 102 and the curved base 105. Referring to FIGS. 1A and 1B, the linear actuating mechanism 103 can include a fastener 109, a first coupler 110 and a second coupler 111. The first coupler 110 can be fixed in alignment with an aperture 113 included in or formed through the planar member 107. The second coupler 111 can be fixed onto the movable member 102, in alignment with the first coupler 110.

In some implementations, the first coupler 110 may include an internally threaded through hole, such as the example that is visible and labeled 110A in FIG. 1B. The first coupler 110 can be fixed to the planar member 107, for example via a welding process, with the internally threaded through hole 110A in alignment with the aperture 113. In an implementation, the first coupler 110 may be configured to support the fastener 109 such that the fastener 109 extends perpendicular relative to the planar member 107. Referring to FIG. 1B, in an implementation, second coupler 111 may have an inner member 110A and outer member 110B and can be fixed, for example via a welding process onto the movable member 102, aligned to the first coupler 110 and may be configured for transferring a linear movement to the movable member 102. In addition, the fastener 109 can be fixed from end to the inner member 111A of the second coupler 111, for example via a welding process.

In some implementations, the fastener 109 can be selected from the group consisting of a screw, a twist, a rivet, and a bolt. Furthermore, the first coupler 110 may be implemented as an internal threaded member, for example a screw nut. In addition, the second coupler 111 may be implemented with a ball bearing having an inner ring, implementing the inner member 111A, and an outer ring, implementing the outer member 110B. Accordingly, the distal end of the fastener 109 can be welded or otherwise secured to the inner ring of the ball bearing and the outer ring of the ball bearing can be welded to the movable member 102. This can serve, for example, two purposes, namely, keeping the movable member 102 in parallel to the fixed arm 104 and preventing from turning the movable member 102 while turning or screwing the fastener 109, thereby constraining the movable member 102 downward-upward movement.

Referring to FIG. 1B, the fastener 109 may have a threaded part 114 and can pass through the aperture 113 with the threaded part in a threaded engagement of the threaded part 114 with the inner threads of the threaded through hole 110A can translate a rotating or turning of the fastener 109 in one direction to a downward movement of the movable member 102 for an ultimate compression of a portion of an exemplary spinal cord that may be placed and encompassed by the movable member 102 and the curved base 105. The threaded engagement can translate a rotating or turning of the fastener 109 in an opposite direction to an upward movement of the movable member 102, to provide for adjustment.

As described, the apparatus 100 includes an arm, such as the fixed arm 104, having a curved base end, e.g., the J-shaped like fixed member 101 and an upper end. The apparatus 100 can include a planar member, e.g., the planar member 107 fixed to the arm 104 at a location proximal the upper end, and can include a movable member, for example the movable member 102 comprising a plate that extends parallel to the planar member, and that includes a lateral opening, e.g., the lateral slit 112 through which the fixed arm can extend. As described, the first coupler 110 can be secured to the planar member, and the second coupler 111 can be secured to the movable member. The apparatus, as described, can also include a rotatable member, such as the fastener 109 having a distal end and coupled by the first coupler to the planar member. As described in the coupling can be in a coupling configuration wherein rotating the rotatable member, e.g., the fastener 109, in a given direction can move the distal end relative to the planar member in a direction toward the curved base end. In an implementation, as described, the distal end of the fastener 109 can be coupled by the second coupler 111 to the movable member in a configuration, for example by fixing to the inner member 110A, such that movement of the distal end of the fastener toward the curved base end in turn moves the movable member toward the curved base end.

In another aspect of the present disclosure, a method is described to develop a unilateral spinal cord compression injury in animal models that can be used for the following studies about SCIs, for example cervical SCIs.

Figure 2:
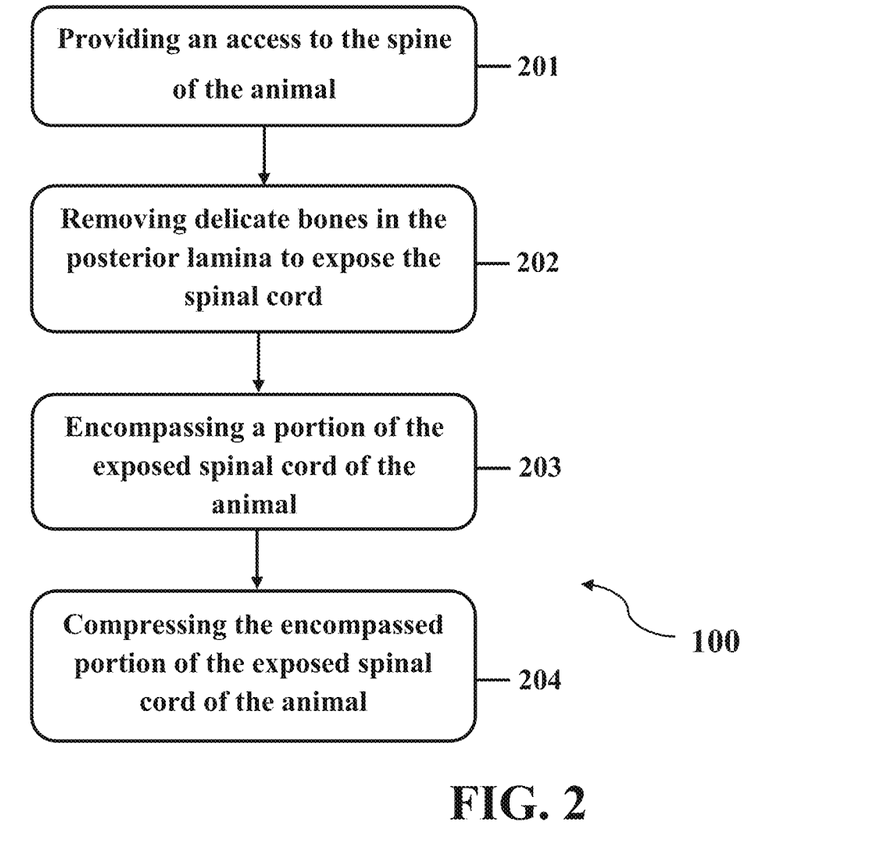
FIG. 2 illustrates an example of a method for applying a unilateral spinal cord injury (SCI) in an animal model, consistent with one or more exemplary embodiments of the present disclosure.

FIG. 2 illustrates an example of a method 200 for applying a unilateral spinal cord injury (SCI) in an animal. The method can include the steps of providing an access to the spine of the animal (step 201), removing delicate bones in the posterior lamina to expose the spinal cord (step 202), encompassing a portion of the exposed spinal cord of the animal (step 203) and compressing the encompassed portion of the spinal cord (step 204).

In some implementations, the animal model may be a mammal animal and may be selected from a group consisting of rabbits, rats, etc.

In the first step 201, an access to the spine of the animal model can be provided, for example, via a surgery in the back of the animal. Moving on to the second step 202, the delicate bones in the posterior lamina may be removed to expose the spinal cord. The removing of the delicate bones can be achieved through a Laminectomy process, which is surgical procedure known to persons skilled in the art for removing a portion of the vertebral bone called the lamina to expose the spinal cord. In the third step 203, a portion of the exposed spinal cord of the animal model may be encompassed to be compressed in the next step 204. The encompassing and compressing of the portion of the exposed spinal cord of the animal model can be done using the apparatus 100 of the present disclosure as described in detail herein above. The portion of the exposed spinal cord of the animal may be half (of the cross-section) of the exposed spinal cord or less. The apparatus 100 can produce graded injury severities, defined by the amount of force applied to the exposed spinal cord, which is effectuated by applying various number of turning or screwing rotations of the fastener 109.

Figure 3:
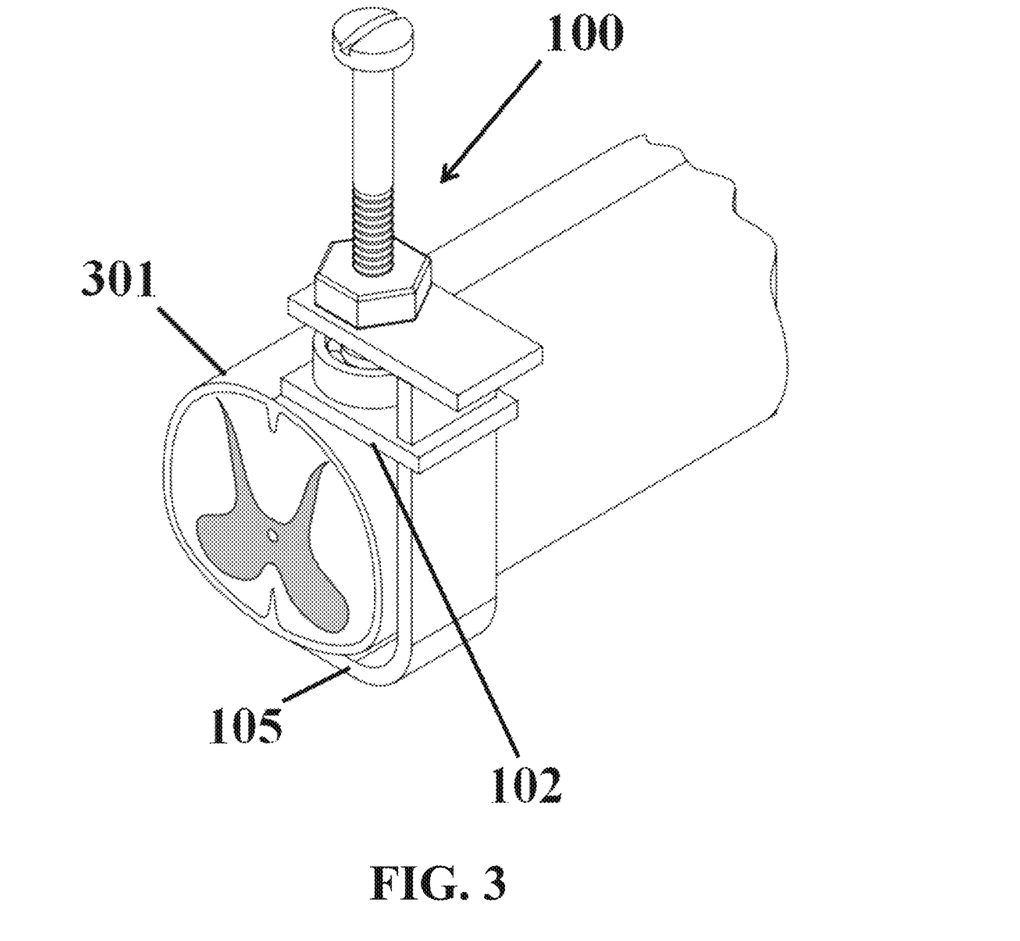
FIG. 3 illustrates one implementation of an exemplary apparatus for unilateral spinal cord compression of a spinal cord encompassing a portion (half or less) of an exemplary spinal cord, consistent with one or more exemplary embodiments of the present disclosure.

FIG. 3 illustrates a schematic structural view of the utility model using an exemplary apparatus for unilateral spinal cord compression, consistent with one or more exemplary embodiments of the present disclosure. After a laminectomy process in step 202, a portion of the spinal cord of the animal model is exposed numerated by 301 in FIG. 3. Subsequently, up to half of the exposed spinal cord 301 is encompassed between the movable member 102 and curved base 105 using the apparatus 100 (step 203) as shown in FIG. 3.

Figure 4:
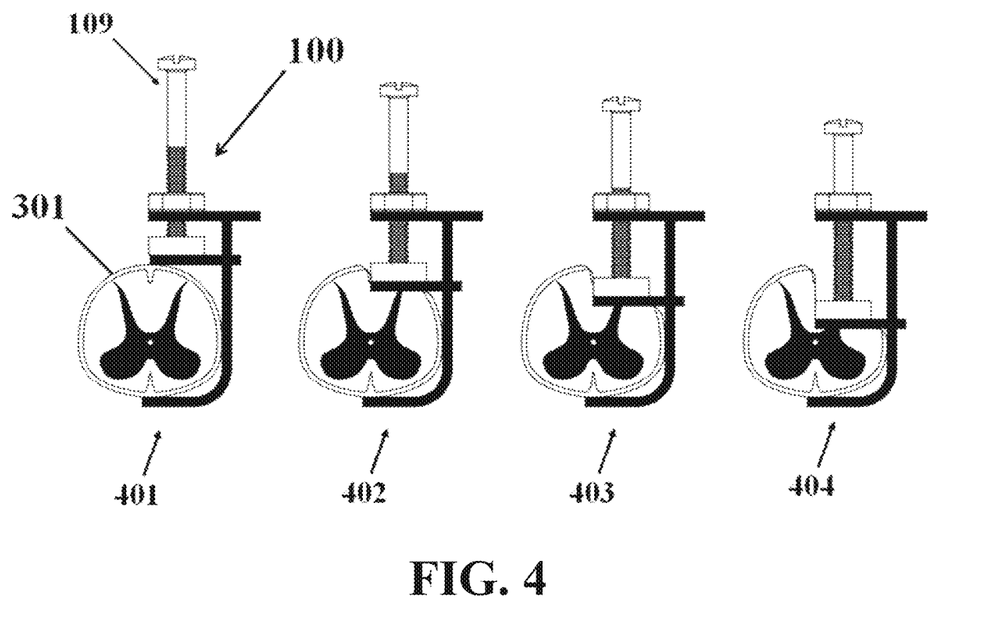
FIG. 4 illustrates example schematic views of encompassing and compressing a portion (half or less) of an exemplary spinal cord in various grades of compression, consistent with one or more exemplary embodiments of the present disclosure.

FIG. 4 illustrates schematic structural views of encompassing and compressing a portion of an exemplary spinal cord (up to half of an exemplary spinal cord) in different grades of compression, consistent with one or more exemplary embodiments of the present disclosure. As shown in this figure, the exposed spinal cord 301 is partially encompassed through step 203 (numerated as 401 in FIG. 4). Subsequently, in step 204, the movable plate 102 moves downward via turning the fastener 109 result in compressing half of the spinal cord or less. Various grades of severity of the applied SCI compression are numerated as 402, 403 and 404 as shown in FIG. 4, which can be controlled by changing the number of turning or screwing rotations of the fastener 109.

In some implementations, the apparatus 100 and method 200 as disclosed here can be applied to prepare and develop a unilateral SCI in an animal model, specifically a unilateral cervical SCI. The developed unilateral SCI model can be used as a quite precise model in clinical studies about the SCI affects and therapeutic treatments, for example drug treatments through comparing two healthy and injured sides of the animal model. The apparatus and method disclosed herein can be used for a precise unilateral compression of spinal cord, without damage to contralateral spinal cord tracts.

EXAMPLES

Example 1

Fabrication of the Apparatus for Unilateral SCI in Rats

Figure 5:
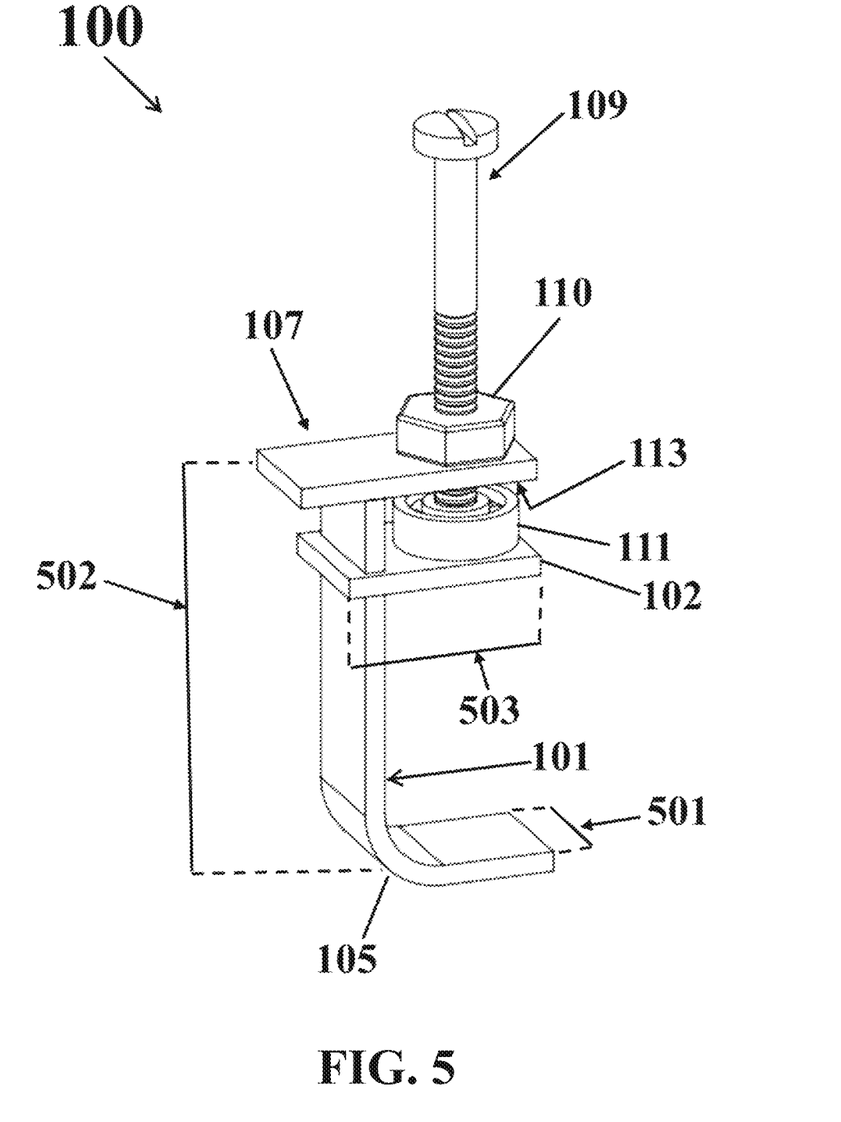
FIG. 5 illustrates an image of an exemplar apparatus fabricated for unilateral spinal cord compression, consistent with one or more exemplary embodiments of the present disclosure.

In this example, a Unilateral Spinal Cord Compression Device was fabricated based on the size and dimensions of the cervical spinal cord of an exemplar adult Wistar rat that can be used for any Wistar rat and also for any animal having a similar spinal cord dimensions. Herein, the targeted Wistar rats have a spinal cord transverse diameter of about 4 mm and a vertical diameter of about 3 mm. A gold sheet with a thickness of about 0.5 mm was used for the fabrication of an exemplar apparatus 100 consistent with the present disclosure. The gold sheet was cut and scraped using a fiber laser cutting machine. As shown in FIG. 5, an exemplar fixed member 101 with a width 501 of about 3 mm and a height 502 of about 10 mm (i.e. 3×10 mm) and an exemplar movable member 102 with a width of about 3.5 mm and a length 503 of about 4 mm (i.e. 3.5×4 mm) were fabricated. The planar member 107 has a length of about 6 mm (i.e. 3×6 mm) and includes an aperture 113 with a diameter of about 1 mm. A stainless steel fastener 109, a nut 110 and a ball bearing 111 were supplied in a desired dimensions (The fastener 109: fillister head, grip length=2 mm, thread length=8 mm, nominal length=10 mm, major diameter=0.5 mm; The nut 110: width across flats=3 mm, width across corn=3.5 mm, thick=1 mm, maximum inner diameter=0.5 mm; The ball bearing 111: inner ring=1 mm, outer ring=3 mm, thick=1 mm). Ultimately, all components were assembled together via a welding process using a laser beam welding.

Example 2

Unilateral Spinal Cord Compression in Wistar Rats

In this example, the capability of an exemplar apparatus and method for unilateral (in this example: left side) spinal cord compression disclosed in the present disclosure was demonstrated to produce graded morphological changes in 12 adult female Wistar rats causing a SCI at their cervical level 5 (C5). Three different seventies of SCI (about 1 mm compression=about 70 Kdyn, about 1.5 mm compression=about 160 Kdyn, and about 2 mm compression=about 280 Kdyn) were performed onto the exposed spinal cord (4 rats in each severity group) for about 2 seconds. Two sham groups (as control groups) were just anesthetized and subjected to laminectomy±device insertion without spinal cord compression (2 rats per groups). The animals were euthanized about 1 hour after surgery, and a sample tissue (about 9 mm portion of spinal cord) was extracted for histological assessments using hematoxylin and eosin staining.

Figure 6A:
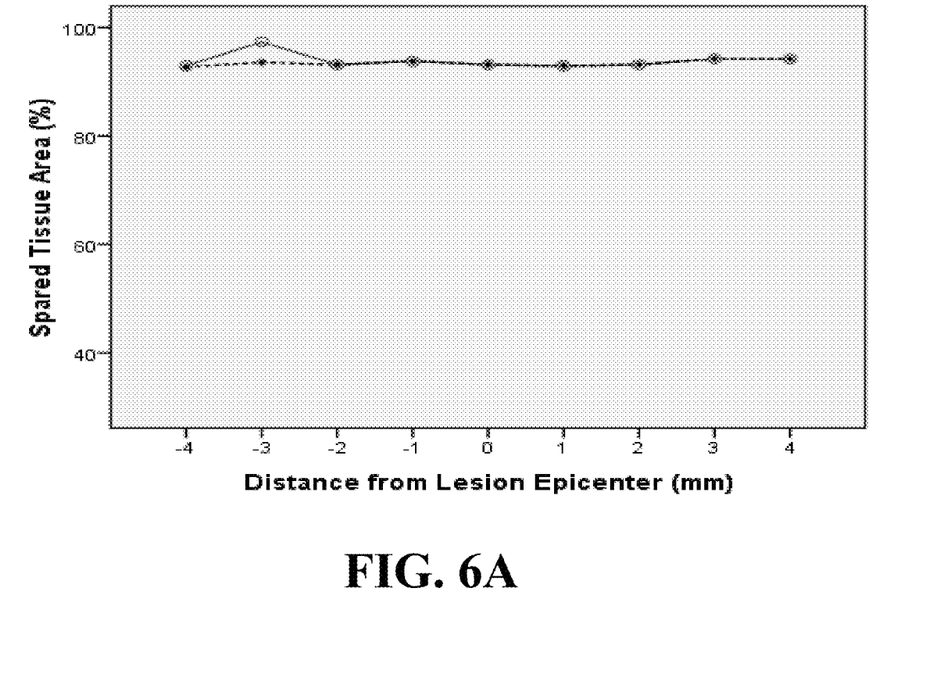
FIG. 6A illustrates the spared tissue area (%) in the right (contralateral) and the left (ipsilateral) hemicords for a first sham group just subjected to laminectomy in connection with example 2.
Figure 6B:
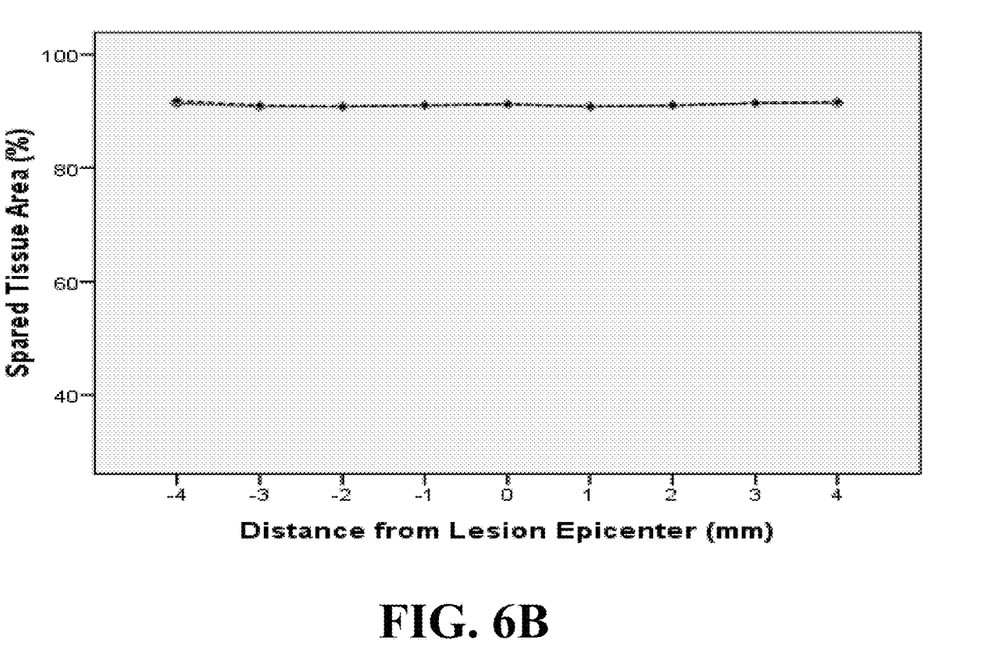
FIG. 6B illustrates the spared tissue area (%) in the right (contralateral) and the left (ipsilateral) hemicords for a second sham group subjected to laminectomy+device insertion in connection with example 2.
Figure 6C:
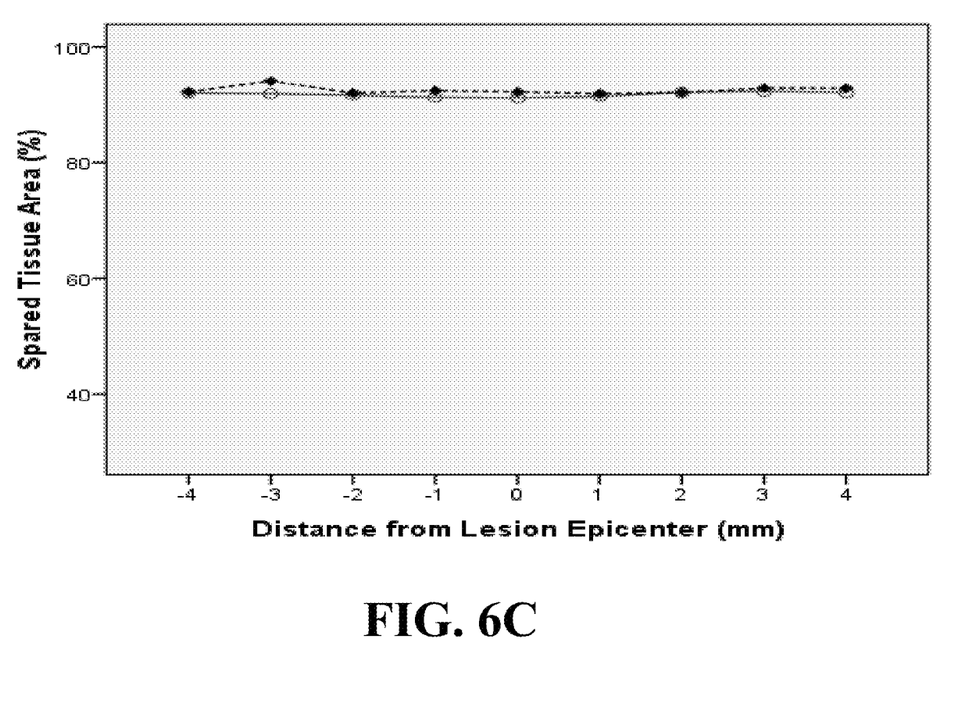
FIG. 6C illustrates the spared tissue area (%) in the right (contralateral) and the left (ipsilateral) hemicords for a group subjected SCI compression of about 1 mm (about 70 Kdyn) in connection with example 2.
Figure 6D:
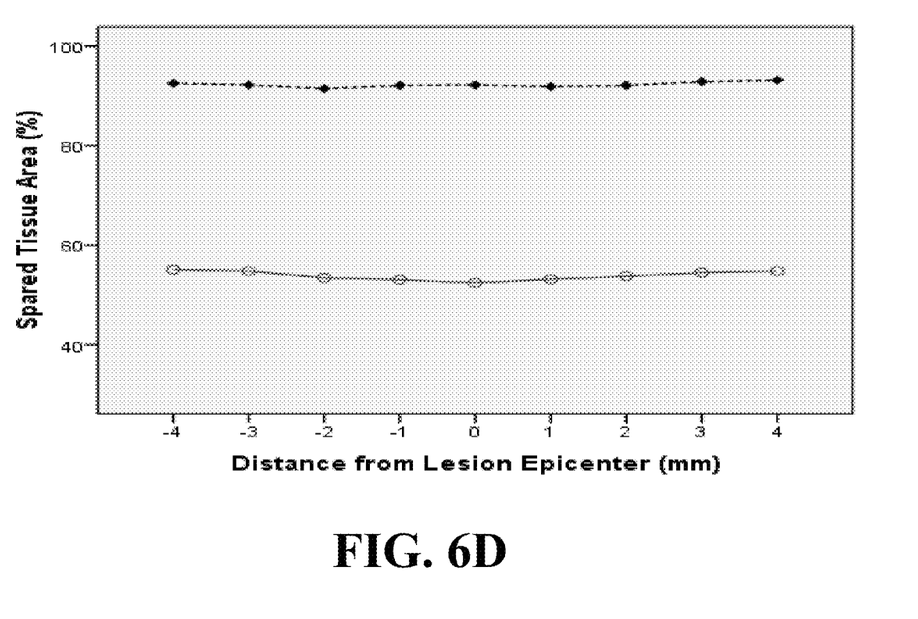
FIG. 6D illustrates the spared tissue area (%) in the right (contralateral) and the left (ipsilateral) hemicords for a group subjected SCI compression of about 1.5 mm (about 160 Kdyn) in connection with example 2.
Figure 6E:
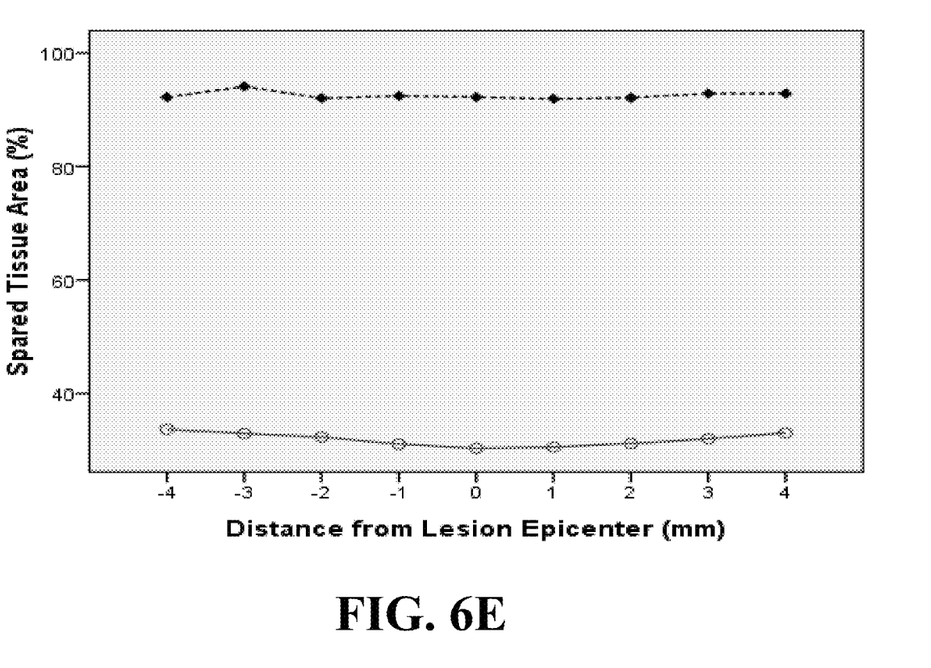
FIG. 6E illustrates the spared tissue area (%) in the right (contralateral) and the left (ipsilateral) hemicords for a group subjected SCI compression of about 2 mm (about 280 Kdyn) in connection with example 2.

FIGS. 6A-6E show the spared tissue area (%) in the right (contralateral) (designated by dashed line) and the left (ipsilateral) (designated by solid line) hemicords in 5 groups, including: a first sham group just subjected to laminectomy (FIG. 6A), a second sham group subjected to laminectomy+device insertion (FIG. 6B) and three groups subjected to SCI compression of about 1 mm (about 70 Kdyn) (FIG. 6C), about 1.5 mm (about 160 Kdyn) (FIG. 6D) and about 2 mm (about 280 Kdyn) (FIG. 6E). It can be seen from these figures that there is no significant reduction of the spared tissue in contralateral spinal cord among all groups.

Referring to FIGS. 6A and 6B, no significant deficit is observable in the laminectomy±device insertion controls. Also regarding to FIG. 6C, there is no significant force-related morphological difference in the compressed half of spinal cord following the 1 mm compression SCI. While according to FIGS. 6D and 6E, a significant decrease in spared tissue area in the left side was happened due to the unilateral compression of more than 1 mm.

Moreover, a statistical analysis showed a significant reduction of the spared tissue in ipsilateral spinal cord followed by 1.5 mm compression ($P<0.01$) and 2 mm compression ($P<0.001$). The least amount of spared tissue was displayed in 2 mm compression SCI that shows a more reliable result.

What is claimed is:

1. An apparatus for unilateral spinal cord compression, comprising:
   a fixed member, comprising:
      a fixed arm having two ends; and
      a planar member having an aperture,
         wherein a first end of the two ends is a curved base end and the planar member is fixed onto a second end of the fixed arm;
   a movable member, comprising a plate parallel to the planar member having a lateral slit to pass through the fixed arm; and a linear actuating mechanism, comprising:
  a fastener, configured to move upward and/or downward through the aperture in a direction toward the curved base end responsive to a screwing movement or a turning movement of the fastener;
  a first coupler fixed around the aperture on the planar member, the first coupler configured to couple the fastener perpendicularly on to the planar member; and
  a ball bearing fixed onto the movable member aligned to the first coupler, the ball bearing configured to:
    couple the fastener to the movable member;
    translate the screwing movement or the turning movement of the fastener to a longitudinal movement of the movable member along the fixed arm; and
    compress a portion of spinal cord encompassed between the movable member and the curved base end responsive to the longitudinal movement of the movable member toward the curved base end.

2. The apparatus according to claim 1, wherein the fixed arm comprises a free edge for engagement with a holder to secure the apparatus.

3. The apparatus according to claim 1, wherein:
  the ball bearing comprises an inner ring and an outer ring,
  the ball bearing fixed from the outer ring onto the movable member aligned to the first coupler and is configured to transfer a linear movement to the movable member,
  the fastener passes through the aperture and a distal end of the fastener is fixed to the inner ring of the ball bearing, and
  the fastener, the first coupler and the ball bearing are configured to translate a rotation of the fastener to a longitudinal movement of the movable member, along the fixed arm.

4. The apparatus according to claim 1, wherein the first coupler comprises an internally threaded through hole, wherein the fastener comprises a threaded portion, wherein the threaded portion has a threaded engagement with the internally threaded through hole.

5. The apparatus according to claim 1, wherein compress a portion of an object encompassed between the movable member and the curved base end comprises compress half of a spinal cord placed between the movable member and the curved base end.

6. The apparatus according to claim 1, wherein the fastener comprises at least one of a screw, a twist, a rivet, and a bolt.

7. The apparatus according to claim 1, wherein the fixed member and the movable member comprise a metal or a metal alloy sheet.

8. The apparatus according to claim 7, wherein the fixed member and the movable member are made of a material comprising at least one of stainless steel, passificated stainless steel grade 314 and gold.

9. The apparatus according to claim 7, wherein the metal or metal alloy sheet has a thickness of less than 1 mm.

10. An apparatus for unilateral spinal cord compression, comprising:
  an arm, having a curved base end and an upper end;
  a planar member fixed to the upper end of the arm;
  a movable member, comprising a plate that extends parallel to the planar member, and having a lateral opening through which the fixed arm extends;
  a first coupler, secured to the planar member;
  a second coupler, secured to the movable member; and
  a rotatable member, having a distal end, and coupled by the first coupler to the planar member in a coupling configuration configured to move the distal end relative to the planar member responsive to rotation of the rotatable member in a given direction, in a direction toward the curved base end, wherein the distal end is coupled by the second coupler to the movable member in a configuration configured to move the movable member toward the curved base end responsive to movement of the distal end toward the curved base end.

* * * * *